United States Patent [19]

Weisz

[11] Patent Number: 5,843,920
[45] Date of Patent: Dec. 1, 1998

[54] ANIONIC SACCHARIDES FOR EXTRACTION OF ANTI-ANGIOGENIC PROTEIN FROM CARTILAGE

[75] Inventor: Paul B. Weisz, State College, Pa.

[73] Assignee: BioCell Technology, LLC, Newtown, Pa.

[21] Appl. No.: 710,375

[22] Filed: Sep. 16, 1996

Related U.S. Application Data

[60] Provisional application No. 60/004,022, Sep. 29, 1995.

[51] Int. Cl.$^6$ .......................... A61K 31/715; A61K 35/34
[52] U.S. Cl. ................................. 514/58; 514/2; 424/548; 424/549
[58] Field of Search ..................... 514/58, 2; 424/548, 424/549

[56] References Cited

U.S. PATENT DOCUMENTS

| | | | |
|---|---|---|---|
| 5,019,562 | 5/1991 | Folkman et al. | 514/58 |
| 5,183,809 | 2/1993 | Weisz et al. | 514/58 |
| 5,262,404 | 11/1993 | Weisz et al. | 514/58 |
| 5,268,384 | 12/1993 | Galardy | 514/419 |
| 5,562,535 | 10/1996 | Puppolo | 452/198 |
| 5,618,925 | 4/1997 | Dupont et al. | 530/400 |

FOREIGN PATENT DOCUMENTS

| | | | |
|---|---|---|---|
| 373540 | 6/1990 | European Pat. Off. | C07K 3/18 |
| WO 94/28020 | 12/1994 | WIPO | C07K 15/00 |

OTHER PUBLICATIONS

Folkman et al, "Control of Angiogenesis with Synthetic Heparin Substitutes", Science 243, Mar. 17, 1989, pp. 1490–1493.

Lee et al, "Shark Cartilage Contains Inhibitors of Tumor Angiogenesis", Science, 221, Sep. 18, 1983, pp. 1185–1187.

Shing et al, "Affinity of Fibroblast Growth Factors for β–Cyclodextrin Tetradecasulfate", Anal. Biochem. 185, 1990, pp. 108–111.

Mizobuchi et al, "Separation of Aromatic Amino Acids on β–Cyclodextrin Polyurethane Resins", J. Chromatog. 208, 1981, pp. 35–40.

Otta et al, "Cyclodextrin–Cellulose Copolymers", Proceed. 4th Int. Symp. on Cyclodextrins, 1988, pp. 139–143.

Folkman et al, "Isolation of a Tumor Factor Responsible for Angiogenesis", J. Exp. Med. 133, 1971, pp. 275–288.

Snow et al, "Sulfated Glycosaminoglycans: A common Constituent of all Amyloids?", Lab. Invest. 56, No. 1, 1987, pp. 120–123.

Komiyama et al, "Immobilized β–Cyclodextrin Catalyst for Selective Synthesis of 4–Hydroxybenzaldehyde", Polymer J., 18, No. 4, 1986, pp. 375–377.

Zsadon et al, "Cyclodextrin Polymers: Types and Specific Properties", Int. Symp. on Cyclodextrins, 1981, pp. 327–336.

Wiedenhof et al, "Properties of Cyclodextrins", Die Staerke, 21, 1969, pp. 119–122.

Grant et al, "Metachromatic Activity of Heparin and Heparin Fragments", Anal. Biochem. 137, 1984, pp. 25–32.

Scott et al, "Differential Staining of Acid Glycosaminoglycans by Alcian Blue in Salt Solutions", Histochemie, 5, pp. 221–232.

Primary Examiner—Kathleen K. Fonda
Attorney, Agent, or Firm—Glenna Hendricks; Stephen Gates

[57] ABSTRACT

Anti-angiogenic protein composition can be prepared simply and efficiently by contacting cartilage particles containing the protein together with an electrolyte solution and an oligosaccharide bearing a minimum number of anionic substituents per sugar unit, to extract the anti-angiogenic protein from the cartilage particles and to form a complex of the oligosaccharide and the protein. The resultant anti-angiogenic complex can be used for therapeutic treatment of various angiogenic and related diseases.

20 Claims, 1 Drawing Sheet

ANIONIC SACCHARIDES FOR EXTRACTION OF ANTI-ANGIOGENIC PROTEIN FROM CARTILAGE

This application derives priority from Provisional Patent Application 60/004,022 filed Sep. 29, 1995.

This invention is directed to compositions that inhibit the pathological growth of blood vessels in mammals, to methods of preparation of such compositions, and to the use of these compositions as therapeutic agents.

BACKGROUND OF THE INVENTION

1. Angiogenesis

It was discovered in the 1970that the growth of tumors in mammals depends on the initiation, growth and continued formation of new capillary blood vessels (J. Folkman et al, "Isolation of a tumor factor responsible for angiogenesis", J. Exp. Med. 133, 275, 1971). The formation of these new blood vessels supports the growth of new tumor cells, just as the same process supports the development of an embryo or the healing of wounds. This process is known as neovascularization or angiogenesis. Agents that emanate from the tumor, for example, cause nearby blood vessels to produce new capillaries that grow towards and to the tumor and provide the nourishment necessary for its further growth. It is now known that the agents that are responsible for inducing neovascularization are growth factor proteins of the fibroblast growth factor (FGF) family. While a great many types of proteins exist and are involved in a large variety of different biological tasks, these growth factor proteins specifically induce proliferation and migration of endothelial cells, which are the cellular building blocks of blood capillaries and vessels. They are pro-angiogenic proteins, therefore. It is now also known that uncontrolled blood vessel growth is a phenomenon involved in pathologies other than in tumor growth. They are referred to as angiogenic diseases (see Battegay, E. J., "Angiogenisis: mechanistic insights, neovascular diseases, and therapeutic prospects", [Review], Journal of Molecular Medicine. 73(7):333–46, 1995). They include for example diseases of the eye, such as corneal neovascularization, diabetic retinopathy and neovascular glaucoma; and other diseases such as hemangiomas, rheumatoid arthritis and psoriasis, among others.

2. Anti-Angiogenic Agents

The above discoveries led to a search for agents that might be used to inhibit angiogenesis. Cartilage, known to resist invasion by blood vessels, does not support the propagation of blood vessels (H. Brem et al, "Inhibition of tumor angiogenesis mediated by cartilage", J. Exp. Med, 141, 427, 1975). Laborious experimental procedures of extraction of cartilage from rabbit, veal or shark have resulted in small concentrations of anti-angiogenic agent (R. Langer et al, Science 193, 70, 1976; R. Langer et al, Proc. Natl Acad. Sci. USA, 77, 4331, 1980; A. Lee et al, Science, 221, 1185, 1983) and have identified the substance to be a protein (M. A. Moses et al, Science 248, 1408, 1990).

The methods for obtaining minute amounts of this anti-angiogenic material have been complex, involving multiple steps of extraction, purification, precipitation, separations involving ion exchange, desalting, chromatographic steps, filtrations, ultrafiltrations, dialysis and the like.

The search for effective and affordable agents that would inhibit angiogenesis, that is for anti-angiogenic materials or formulations that would counteract the influence of pro-angiogenic proteins, has been continuing since these findings were made. Examples are the formulations of heparin with certain steroids (J. Folkman et al, Science 221, 719, 1983), fumagillin (see U.S. Pat. No. 5,135,919 and the combination of sulfated cyclodextrins with specific steroids (Folkman et al, U.S. Pat. No. 5,019,562). The latter discovery poses significant background for the present invention, because it required formulation of the cyclodextrin agents with a steroidal or similar agent, without which the sulfated cyclodextrin would actually be pro-angiogenic, i.e., it would aggravate angiogenesis rather than inhibit it. Furthermore it was shown that the cyclodextrins having high anionic density will chemically complex pro-angiogenic proteinic growth factors (Y. Shing et al, Anal. Biochem. 185, 108, 1990) and can be used to capture and separate the pro-angiogenic factors (Weisz et al, U.S. Pat. No. 5,183,809).

Thus obtaining an effective naturally occurring anti-angiogenic agent from cartilage in useful concentration and quantity continues to be a highly desirable goal.

SUMMARY OF THE INVENTION

I have found that the anti-angiogenic protein present in natural cartilage can be extracted and concentrated, either as a solid composition or in soluble form, by a simple, inexpensive process. The extraction is done by intimately contacting solid particles of cartilage, a composition having a high intramolecular concentration of anion substituents and a solution of an electrolyte having a controlled concentration. The natural anti-angiogenic protein is transferred from the cartilage as a donor to the composition as a receptor. The resultant protein-receptor complex is separated from the cartilage particles to form an anti-angiogenic composition, either as a solid or solubilized in an aqueous solution, to form a concentrated anti-angiogenic protein product.

The complexes themselves, or solutions containing the anti-angiogenic protein can be readily administered by various means to treat diseases requiring control of blood vessel formation.

DETAILED DESCRIPTION OF THE INVENTION

3. The Method

Figure 1:
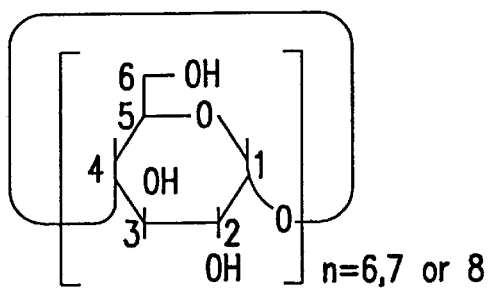
FIG. 1 is a schematic representation of the chemical structure of alpha, beta or gamma cyclodextrins useful in the invention.

Animal cartilage is a unique source of protein, characterized by its anti-angiogenic capability to inhibit endothelial cell migration and proliferation and blood vessel generation, in contrast to the many known pro-angiogenic proteins, such as FGF and other growth factors that promote endothelial cell proliferation and migration. It is readily available from mammals, such as shark, in great abundance. It can be extracted from cartilage and transferred to a highly anionic acceptor substance in the presence of an electrolyte solution of a particular concentration.

While this invention focuses mainly on extraction of anti-angiogenic protein from cartilage, it must be understood that other biological material containing such protein can be found, and the method taught by this invention may be used. However, other biological material generally has a large variety of proteins associated with it, including so-called growth factor proteins, which are pro-angiogenic, such as FGF. Thus additional steps of separation would be required to separate the desired anti-angiogenic agent. Thus the present method preferably is carried out with cartilage particles.

In order to extract the anti-angiogenic protein from natural cartilage, finely divided particles of cartilage are contacted with a solution containing a saccharide having a minimum number of anionic substituents such as sulfates, and a particular concentration range of electrolyte, for a sufficient time to cause the transfer of substantial amounts of the anti-angiogenic protein from the cartilage to the anionic receptor. The electrolyte concentration is chosen to be high enough to displace the protein from the cartilage, while below the concentration at or above which the protein will not adhere or complex with the anionic receptor. The minimum number of anionic substituents on the receptor, preferably a saccharide, is chosen to assure strong protein absorption on the saccharide, while the type and concentration of the electrolyte is chosen to afford desorption of the protein from the cartilage particles.

After intimate contact of the cartilage donor and the saccharide receptor in the electrolyte solution, preferably with agitation, has been provided for an adequate period of time, the cartilage particles are separated from the solution containing the extracted protein complexed to the saccharide. Any precipitated protein/saccharide complex may be obtained by settling or centrifuging and washing. any complex remaining in solution can be desalted by dialysis and concentrated by evaporation or lyophilation.

In the preferred method of this invention, an anionic saccharide is chosen that is in solid particulate form. Thus, after the complexing procedure as described above, separation of the now solid saccharide/protein complex is easily achieved. For example, by choice of different ranges of particular size for the cartilage and for the saccharide particulates, separation is achieved by appropriately sized sieves. The choice of a solid protein acceptor is particularly advantageous because the anti-angiogenic protein product is now localized on the separated and easily washable solid, avoiding the need for costly techniques for removing the electrolyte and the need for considerable volumes of water to obtain a pure and concentrated protein product.

In a typical preferred practice of this invention, cartilage particles, divided to a particle size of about 200–400 microns, and the receptor particles are stirred together in an electrolyte solution. A comparatively large difference in particle size between the cartilage and the receptor particles leads to easy separation of the particles after extracting and complexing using appropriately sized sieves.

The particles of the receptor and animal cartilage are added to a dilute aqueous electrolyte solution, such as sodium chloride, at a concentration of electrolyte of 0.2–4 molar. An optimal concentration for monovalent anions is about 0.9 to 4 molar, whereas divalent ions are preferably employed as 0.2 to 1.0 molar solutions. Various electrolytes are useful herein, including salts of sodium, potassium, lithium, magnesium, calcium and the like. Thus although the chlorides are preferred, other salts can be used. The optimal concentration may vary with the particular receptor employed, e.g., an oligosaccharide, and the electrolyte employed. The suitability of the electrolyte solution concentration may be determined by adsorption of the receptor by a dye, as will be further explained hereinbelow, and should be less than that concentration at which appreciable dye adsorption occurs. Too low a concentration however will result in lengthy transfer times for the anti-angiogenic protein.

The mixture of particles and electrolyte are stirred or agitated together for a time sufficient to transfer substantial and desired amounts of protein from the cartilage particles to the anionic receptor particles.

The cartilage and receptor particles are then separated by methods such as controlled settling (large particles first), centrifugation or filtering using appropriate pore size screens, or by elutriation. When the particle sizes of the cartilage and the receptor have been chosen to be quite different, they can be separated readily using different size screens.

It is also possible to employ sufficiently small particles of the anionic receptor solid, and sufficiently large particles of the cartilage (donor) solid, so that the former, in the manner of a fine dispersion, can circulate through the interstices of a retained bed of the cartilage solid. After a sufficient length of time of contact, the fine dispersion, now bearing complexed protein, can be "washed out" of the retained bed for collection.

In another variant of the method, both types of solids are retained in separate beds by appropriately sized screens or membranes, and the electrolyte containing solution is circulated around and through both beds to afford contact and transfer of the protein.

When the receptor used is a soluble compound, the resulting receptor-protein complex is obtained from solution. Excess electrolyte can be removed by ion exchange, dialysis, use of micromolecular filters and the like in known manner. The complex may be further concentrated or purified if desired. For example, the solution can be evaporated or freeze dried to remove water. The complex can be purified by molecular size chromatography to separate high molecular weight complexed products from non-complexed receptor, e.g., oligosaccharides, and other low molecular weight products.

The complex may be used itself as a therapeutic agent, or the anti-angiogenic protein may be separated from the receptor or oligosaccharide by treatment with a strong (over 1 molar) electrolyte solution and further steps of separation.

The use of solid particles of an oligosaccharide is preferred herein, however, because of the unique advantages and simplification of the separation procedures. When it is desired to produce the anti-angiogenic protein by itself, apart from its complex with a solid saccharide, this can be accomplished by treatment with a highly concentrated electrolyte, but the separation of the saccharide material thereafter is accomplished by simple mechanical manipulation, such as sieving, screening, settling, decanting and the like.

The extraction and separations described above are preferably carried out at low temperature, to prevent damage to the extracted protein. Room temperature is preferred. However, a slightly lower or higher temperature, i.e. 15°–50° C., may enable extractions or de-salting to proceed more efficiently.

Although the exact mechanism for the present method of preparation is not known with certainty, it is believed that the receptor oligosaccharides, having a minimum anionic concentration, offers a competitively stronger bonding or complexing strength for the anti-angiogenic protein than does the complexing partner that exists in natural cartilage; and the electrolyte having a required concentration in the transfer fluid, provides sufficient force to dissociate the cartilage-protein bonding without substantially interfering with the subsequent oligosaccharide bonding, thereby accelerating the rate of transfer of the protein in a practical period of time.

4. The Protein-Receptor Compositions

The compounds or materials useful in and characteristic of the invention comprise molecules with a high intramolecular density of anionic substituents. They may be organic compounds, monomers such as suramin, or oligomers or polymers, synthetic or natural products, that have or are modified to have, the required high anionic density. I have found certain methods to determine the suitability, i.e., the existence of sufficient anionic density, to serve the methods of this invention. These methods are described further below.

Saccharide-based materials are preferred because of their low cost, ready availability in quantity, and because of their general acceptability in biological systems. The oligosaccharides useful herein may be linear, branched chain or cyclic oligosaccharides. Hydroxy groups of such oligosaccharides are substituted with a minimum number of anions, such as sulfate, phosphate, sulfonate or carboxylate groups and the like. They can also include glycosaminoglycans (GAG), such as heparin or heparin derivatives including compositions referred to as low molecular weight heparins. The oligosaccharides useful herein have been reacted with or contain anions so that a minimum number of anionic substituents per sugar molecule is present.

Figure 2:
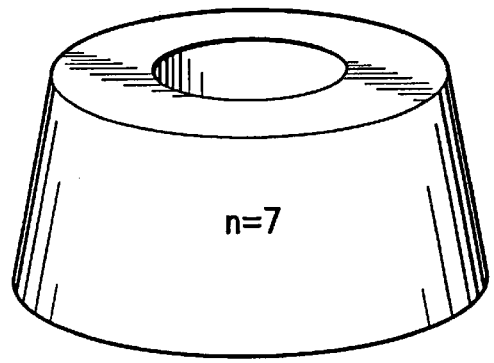
FIG. 2 is a three-dimensional view of alpha, beta and gamma cyclodextrins useful in the invention.

The preferred oligosaccharides are cyclodextrins, their isomers and homologs. These are low molecular weight cyclic oligosaccharides having at least 5 sugar units. Their structure is shown in FIGS. 1 and 2. FIG. 1 is a schematic illustration of the chemical structure of alapha, beta or gamma cyclodextrins. FIG. 2 is a three-dimensional view of the alpha, beta or gamma cyclodextrins useful herein. Generally the cyclodextrins preferred herein have 6–8 sugar units. These molecules, being cyclic, do not have terminal sugar groups, increasing their stability. Sulfated oligosaccharides are generally preferred.

Anionic saccharides are generally water soluble. While it is within the scope of the present invention to employ the step of contacting the cartilage with a soluble species for protein extraction, sparsely soluble or substantially insoluble forms are preferred, as noted above, inasmuch as this provides substantial simplification of separation. For this purpose, the saccharides, or other highly anionic receptor compositions, are employed in the form of polymers or copolymers, or bound to solid surfaces through chemical or ionic linkage units. Methods of polymerization or cross-linking are well known in the chemical and polymer arts. For example, cyclodextrin particles have been obtained by known methods of polymerization; e.g., see N. Wiedenhof et al, Staerke, 21, 119, 1969; cyclodextrin polymeric solids can be obtained in various particle sizes and properties, e.g., B. Zsadon et al, 1st Intern. Symp. on Cyclodextrin, 327, 1981; M. Komiyama et al, Polymer J. 18, 375, 1986; and U.S. Pat. No. 5,075,432. The critical anionic substituents can be added by treatment with a sulfating agent. This is shown in U.S. Pat. No. 5,183,809, wherein the polymer was one of beta-cyclodextrin monomers linked through epichlorohydrin as the cross-linking agent, resulting in solid particles that are subsequently reacted with a sulfating agent such as chlorosulfonic acid, or trimethylamine/sulfate trioxide, so as to introduce that number of anionic sulfate groups to obtain the desired number of sulfate groups per monomer useful in the present method. While saccharides, and particularly cyclodextrin-derived materials are preferred for use in this invention, it is to be understood that other materials offering high anion density, such as resins and others, may be useful as protein receptors in the methods herein described. See for example U.S. Pat. No. 5,183,809 of Weisz et al. Dextran sulfate polymer can be similarly produced by linkage with epichlorohydrin, for example, prior to sulfating. Similarly, sparsely soluble or insoluble saccharides, already in particulate or solid form, such as starches or cellulose, may be employed after sulfation by suitable sulfating agents. Alternatively, copolymers of cyclodextrins with other materials, or linked to other solids, including cellulose, silica and other solid surfaces, may be employed, e.g., chlorodextrin/cellulose of Otta et al, Proc. 4th Inter. Symp. on Cyclodextrins, 139, 1988 or cyclodextrin/polyurethane, of Y. Mizobuchi et al, J. of Chromatography, 208, 35, 1981.

5. The Anion Density for the Compositions of the Invention

As discussed above, the degree of anionic substitution, preferably by sulfate ions, or more appropriately, their intramolecular density, is important. The anionic density required may vary somewhat with the size and structure of the saccharide molecule employed. For example, the preferred cyclodextrins will generally require a minimum of about 1.2 sulfate groups/sugar unit. When sulfation is performed on only one side of the toroidal cyclodextrin molecule, they require a minimum of about 1.0 anions/sugar unit. A linear oligomer of sugar units of more than about five sugar units, for example glucose units, requires a minimum number of about 1.4 or more anions per sugar unit. An example is dextran sulfate. Shorter chains of saccharides require a higher minimum, with a disaccharide requiring more than about 3.5 anions per sugar unit. Such a sulfated saccharide is exemplified by sucrose octasulfate.

I have further found that the satisfactory achievement or presence of the minimum anionic density can be probed by their interactions with specific dyes. One is the shift in spectral color of the dye Azure A, known as metachromasia. Another test reaction makes use of the spectral color change or staining reaction of the dye Alcian Blue when reacted with the anion-substituted composition. In either or both of these tests, the candidate protein-acceptor composition for use herein should closely follow the like reactions of heparin.

The test for metachromasia using the cationic dye Azure A has been described by Grant et al, "Metachromatic activity of heparin and heparin fragments", Anal. Biochem. 137, 25–32, 1984. This test is used to probe the adequacy of saccharide receptors for the purposes of this invention. Again, the amount of metachromasia should be similar to that of heparin.

The test technique of Alcian Blue staining is described by Scott et al, "Differential staining of acid glycosaminoglycans (mucopolysaccharides) by Alcian Blue in salt solutions", Histochemie 5, 221–225, 1965; and by Snow et al, "Sulfated Glycosaminoglycans: A common constituent of all amyloids", Lab. Invest. 56, 120–123, 1987. It determines at what concentration an electrolyte such as magnesium chloride the test material will no longer stain. The technique is used in tissue histology. The most resistant substance, withstanding the highest electrolyte concentration, is heparin. Our criteria again is that the test results show that the protein acceptor is similar or equal to heparin.

When the composition of the invention is a solid, staining can be observed directly. When the composition is soluble, a drop of its solution can be placed as a spot on paper or on a thin layer chromatography plate of alumina and dried. Staining can then be tested by a wetting solution of Alcian Blue dye with various strengths of electrolyte passed by the spot.

These tests are useful because the above cationic dyes complex with the acceptor materials like proteins. The dyes are thus "models" for the complexation of proteins.

6. The Range of Electrolyte Concentration

As discussed hereinabove, there is a range of concentration of the electrolyte useful herein for the simultaneous contact with cartilage and with the protein receptor. The required or optimal electrolyte concentration for the present method will be between about 0.9 to 4.0 molar for monovalent ions (Na, K, Li) and between about 0.2 and 1.0 molar for divalent ions (Ca, Mg). The optimal concentration may best be determined empirically, as it will depend on the combination of the particular oligosaccharide or other acceptor composition and the species of electrolyte used. A useful guide is obtained by the staining test as described above for Alcian Blue. The proper electrolyte concentration useful for the extraction method herein should be below that concentration at which appreciable dye staining occurs. However, lowering the electrolyte concentration will require a longer period of time to achieve appreciable transfer of protein.

7. The Cartilage Protein

The protein useful herein is an anti-angiogenic protein, characterized by its ability to inhibit endothelial cell migration and endothelial cell proliferation, in contrast to the many pro-angiogenic proteins such as FGF and other growth factors that promote endothelial cell proliferation and migration. Testing for the successful extraction or presence of the anti-angiogenic protein can be readily accomplished by independent in vitro tests in endothelial cell cultures, by virtue of successful reduction or inhibition of endothelial cell growth in culture.

8. The Product Compositions

The method of this invention results in the generation of novel and unique compositions with unusual utilities. The products include compositions that are complexed with anti-angiogenic proteins. The preferred complexes are anti-angiogenic proteins complexed with oligosaccharides. Preferably the complexes are solid particles or low solubility particles in aqueous solution. Although the anti-angiogenic protein may also be obtained per se by the further steps of de-complexation and separation, these complexed compositions are themselves highly useful therapeutic agents. When such a complexed composition is introduced to an environment free of the protein of the complex, the complexed anti-angiogenic protein will slowly leak out by de-complexation, as required by the laws of equilibrium. Further, if the biological environment contains other proteins, including FGF or other pro-angiogenic proteins, they will compete for complexation and thereby accelerate desorption of more of the anti-angiogenic protein into that biological environment. The complexed agent of this invention constitutes a pharmaceutical, anti-angiogenic agent. It is also a vehicle for delivery of the active agent which can be targeted to the biological environment where it is needed. The complexing agent, such as an oligosaccharide and preferably a sulfated cyclodextrin, complexed with the anti-angiogenic protein, is targeted to the biological site where it is needed, and slow delivery of the anti-angiogenic protein by equilibrium desorption proceeds at the site of introduction.

The products of the present invention can be administered for therapeutic purposes in known manner. The complexed product per se is a solid and it may be also used in the form of a suspension. The extracted product can be used in solution as a dilute aqueous or salt solution.

For treatment of tumors, the compositions of the invention inhibit the growth of tumors and thus can be administered topically as a solution, e.g., intravenously or subcutaneously. Compositions of the invention in the form of solutions or dispersions of solid particles can be delivered in the form of an ointment or gel for treatment of skin carcinomas. Fluid delivery of soluble compositions can be used to deliver the composition to tissue surrounding a tumor.

For treatment of arthritic joints, the compositions of the invention can be applied topically in solution or as a dispersion in the form of a gel or cream. Solutions of the invention may be injected into the sinovial fluid around the affected joint.

For treatment of diseases of the eye, soluble compositions of the invention may be formulated as eye drops for direct administration to the eye.

For treatment of gastrointestinal tract diseases, solid compositions of the invention can be administered orally in a carrier that will survive stomach acidity, and then be absorbed into the blood plasma.

For treatment of bronchial or pulmonary diseases, the dry or wet compositions of the invention can be nebulized and inhaled, or made into a spray solution.

The invention will be further illustrated by the following examples. However, the invention is not meant to be limited to the details described therein.

EXAMPLE 1

A sample of beta=cyclodextrin was sulfated using trimethylamine/$SO_3$ complex to obtain a mixture of beta-cyclodextrin sulfates (CDS). The mixture was passed over a sephadex column to yield separate fractions containing cyclodextrin with varying average sulfate content, which then was determined by elemental analysis. The following materials were obtained: CDS with about 7 sulfate groups, CDS-7; and beta-cyclodextrin with about fourteen sulfate groups, CDS-14. After impregnating a spot on a thin layer chromatography plate of alumina with a drop of solution of each agent which was then dried, the staining ability of that spot with a solution of Alcian blue dye with various strengths of electrolyte ($MgCl_2$) was tested. An unsulfated beta-cyclodextrin (CD) was also tested, as was heparin. Table I summarizes the data obtained.

TABLE I

| Saccharide Compound | Concentration mg/ml | No Staining at $MgCl_2$ Concentrations: |
|---|---|---|
| CD | 0.8 | any |
| CDS-7 | 0.8 | any |
| CDS-7 | 2.4 | any |
| CDS-14 | 0.8 | >1.0 molar |
| Heparin Control | 0.8 | >1.0 molar |

Thus CDS-14 stains as strongly as heparin. No staining was obtained with CDS-7, even at a three-fold higher concentration.

Thus a cyclodextrin sulfate with about 14 sulfate groups is a capable protein absorber, and demonstrates the need for a minimum number of sulfate substituents.

EXAMPLE 2

Another series of beta-cyclodextrin sulfates having various amounts of sulfate substitution were obtained by sulfating the cyclodextrin and separating the products. After sulfate analysis, they were subjected to the metachromasia test with the dye Azure A described hereinabove. The results are summarized below in Table II.

TABLE II

| Number of Sulfate Substituents per cyclodextrin | Metachromatic Activity |
| --- | --- |
| 0 | 0 |
| 2.3 | 0.1 |
| 4.0 | 0.1 |
| 6.0 | 0.15 |
| 10.4 | 0.95 |
| 14 | 0.98 |
| 15.8 | 0.97 |
| heparins | 0.9–1.0 |

The results identify samples having adequate complexing capability for the methods of this invention. They are the saccharides having a sulfate density greater than 6, and preferably 10 or more.

EXAMPLE 3

This example demonstrates the capability of the receptor oligosaccharide CDS-14 for its successful capability to complex a protein.

When two substances are mixed and placed into an electrical conductivity device in varying proportion with another substance, the conductivity is known to be the linear average of the conductivity of each of the two substances alone. However, if the substances interact by complex formation, a strong deviation from that average will be noted.

Using a standard conductivity probe and a total concentration of protamine and of CDS-14 of 4 mg/ml, the conductivity of protamine (100%) was observed to be 1280 micromhos. The conductivity of CDS-14 was 880 micromhos. Thus one would expect that a 50:50 mixture of the two components would have a conductivity half-way in between, or 1080 micromhos, if no complexing occurs. The observed conductivity however was 1250 micromhos, showing a strong electrostatic complexing of CDS-14 with the protein.

EXAMPLE 4

This example illustrates the extraction method of this invention.

Particles of cyclodextrin sulfate polymer (CSP) are dried under vacuum and ground to a particle size of about 3–10 microns. Cleaned animal cartilage having a particle size of about 1 mm (100 grams) and 2 grams of CSP as above are added to an aqueous solution of 0.6 molar NaCl. The particles are agitated for 60 hours at 30° C.

The larger cartilage particles are allowed to settle by sedimentation during mild stirring.

The CSP-containing fluid is decanted, with additional CSP washed from the bed of sieve supported CAC. The CSP-containing fluid was filtered and the solid CSP product, now associated with extracted and complexed protein, is collected. This product is dispersed in aqueous nutrient and is added to an endothelial cell culture. The CSP product reduces endothelial growth rate in that culture compared to a control culture.

EXAMPLE 5

The protein is extracted from a sample of the CSP product of Example 4 by exposing the product to a solution of 4M NaCl for 12 hours and separating from the solution by filtration. The solution is dialyzed and lyophilized to remove the electrolyte and to obtain a concentrated protein solution. A small sample of the protein product is added to an in vitro cell culture of endothelial cells. The protein strongly inhibits cell proliferation.

EXAMPLE 6

Part A

Dextran sulfate (DS8000), heavily sulfated gamma-cyclodextrin and maltosyl beta-cyclodextrin sulfate were exposed to Azure A dye solution. They exhibited strong metachromasia.

Each sample was analyzed and was found to have a sulfur content greater than about 1.4 sulfate groups per sugar unit.

Part B

Unsulfated dextran, methylated cyclodextrin and hydroxypropyl cyclodextrin were subjected to the same test and did not exhibit metachromasia under the same conditions.

Thus only the three heavily sulfated saccharides were shown to be operable as protein receptors in the method of the present invention.

EXAMPLE 7

100 Grams of CAC particles are immersed in 150 ml of an aqueous solution of 0.6M NaCl electrolyte and 1 g of dissolved beta-cyclodextrin having about 12 sulfate substituents per molecule of CDS is added. The mixture is agitated for 48 hours.

The solution, having dissolved CDS with complexed protein, is separated by filtration, the electrolyte is removed by dialysis, and the volume is reduced by lyophilization.

Samples of the product contain anti-angiogenic protein. The samples added to endothelial cell cultures inhibit cell growth compared to a control culture.

EXAMPLE 8

This example demonstrates the utility of a saccharide/protein complex of the invention to be useful as a therapeutic vehicle for delivery of the protein, i.e., to absorb the protein and subsequently to desorb the protein to a fluid that is devoid of that protein.

A sample of CDS was immersed in a weak solution of Azure A and of bFGF protein to observe the time course of sorption. Upon reaching a saturated state, the polymer was then exposed to a clear aqueous phase and the progress of desorption was observed.

Figure 3A:
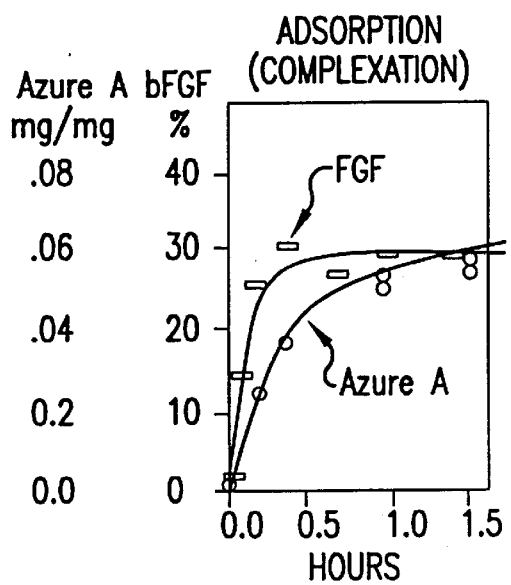
FIG. 3A is a graph demonstrating the process of adsorption of the protein FGF from the surrounding fluid by a solid cyclodextrin sulfate complexing agent.
Figure 3B:
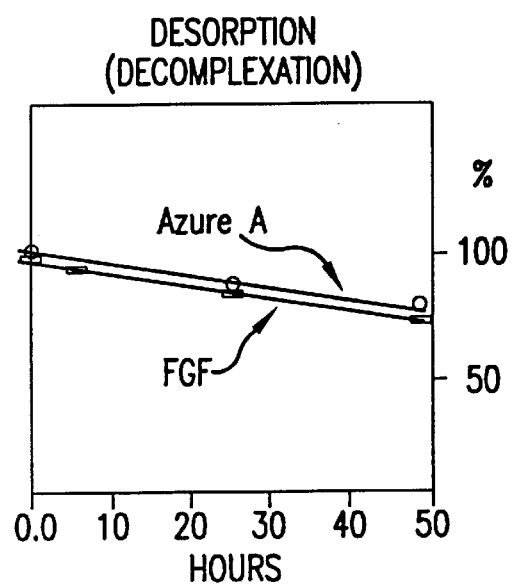
FIG. 3B is a graph demonstrating the process of desorption of the protein into the surrounding protein-free fluid from the solid cyclodextrin sulfate complexing agent that was previous charged with the protein of FIG. 3A.

The results are shown in FIGS. 3A and 3B. FIG. 3A shows the ability of the sulfated oligosaccharide, once complexed by absorption, to slowly and steadily deliver its charge to an aqueous environment by desorption (decomplexation) as shown in FIG. 3B.

Although the present compositions and methods of treatment have been described in terms of specific embodiments, the invention is not meant to be limited except by the appended claims.

I claim:

1. A method of extracting an anti-angiogenic protein from cartilage comprising the steps of:

contacting particles of cartilage with (a) a saccharide having a suitable degree of intramolecular density of anionic substituents and (b) an aqueous medium containing between 0.2 and 4.0 molar concentration of inorganic cations for a time sufficient for anti-angiogenic protein transfer from the cartilage to the saccharide to form a composition, and separating said composition containing extracted anti-angiogenic protein.

2. A method according to claim 1 wherein said composition is soluble in said aqueous medium.

3. A method according to claim 1 wherein said composition is a substantially insoluble composition in the form of porous particles suspended in said aqueous medium.

4. A method according to claim 1 wherein said anionic substituents are chosen from the group consisting of phosphate, sulfate, sulfonate and carboxylate.

5. A method according to claim 1 wherein said composition is capable of combining with a metachromatic dye including Azure A and Alcian Blue as evidenced by standard techniques of metachromasia or staining.

6. A method according to claim 1 wherein the molar concentration of inorganic cations is chosen to be below that which prevents metachromasia of said composition when contacted with Azure A and staining when contacted with Alcian Blue.

7. A method according to claim 1 wherein said saccharide is a sulfated oligosaccharide.

8. A method according to claim 7 wherein said sulfated oligosaccharide is a cyclodextrin including at least about seven sulfate substituents per molecule.

9. A method according to claim 3 wherein said saccharide is a polymer or copolymer of monomers of high intramolecular density of anionic substituents selected from the group consisting of sulfate, phosphate, sulfonate and carboxylate.

10. A method according to claim 9 wherein said monomers are cyclodextrins.

11. A method according to claim 9 wherein said substituted monomers are sucrose octasulfates.

12. A method according to claim 9 wherein said substituted monomers are cyclodextrin sulfates.

13. A method according to claim 9 wherein said monomers are dextran sulfates.

14. A method according to claim 3 wherein said composition is a substantially water-insoluble salt of the saccharide having high intramolecular density of anionic substituents selected from the group consisting of sulfate, phosphate, sulfonate and carboxylate.

15. A method according to claim 3 wherein said composition is in particulate form and is provided in a range of particle sizes distinct from the particle size range of cartilage particles so as to permit separation by mechanical means.

16. A method according to claim 15 wherein said separation is obtained using said mechanical means.

17. A method according to claim 3 wherein said composition particles are in intimate admixture with the cartilage particles and the aqueous medium is moved through said particles.

18. A method according to claim 3 wherein said composition particles and said cartilage particles are separated and the aqueous medium is circulated through all of the particles.

19. A method of extracting an anti-angiogenic protein from cartilage comprising the steps of:

contacting particles of cartilage with a composition containing a saccharide having a suitable degree of intramolecular density of anionic substituents and an aqueous medium containing from about 0.2 to 4.0 molar concentration of inorganic cations, allowing sufficient time for the anti-angiogenic protein from cartilage particles to complex with said saccharide, separating saccharide complexed with protein, then removing said anti-angiogenic protein from the saccharide/protein complex by contacting the solution containing said complex with an inorganic salt at sufficiently high salt concentration to release the protein from the complex.

20. A method of claim 14 wherein the saccharide is cyclodextrin.

* * * * *